(12) United States Patent
Pursley

(10) Patent No.: US 9,192,742 B2
(45) Date of Patent: Nov. 24, 2015

(54) MEDICAL TUBING AND ASSOCIATED DEVICES, SYSTEMS, AND METHODS

(71) Applicant: Volcano Corporation, San Diego, CA (US)

(72) Inventor: Matt D. Pursley, Alpharetta, GA (US)

(73) Assignee: Volcano Corporation, San Diego, CA (US)

( * ) Notice: Subject to any disclaimer, the term of this patent is extended or adjusted under 35 U.S.C. 154(b) by 372 days.

(21) Appl. No.: 13/650,944

(22) Filed: Oct. 12, 2012

(65) Prior Publication Data
US 2013/0123752 A1 May 16, 2013

Related U.S. Application Data

(60) Provisional application No. 61/547,661, filed on Oct. 14, 2011.

(51) Int. Cl.
*A61M 35/00* (2006.01)
*A61M 25/00* (2006.01)
*A61M 39/08* (2006.01)

(52) U.S. Cl.
CPC ....... *A61M 25/0043* (2013.01); *A61M 25/0009* (2013.01); *A61M 25/0053* (2013.01); *A61M 39/08* (2013.01); *A61M 25/0012* (2013.01); *Y10T 29/4987* (2015.01); *Y10T 29/49826* (2015.01); *Y10T 29/49885* (2015.01);
(Continued)

(58) Field of Classification Search
CPC ..................... A61M 25/0043; A61M 25/0053; A61M 25/0009; A61M 39/08; A61M 25/0012; A61M 2025/0034; A61M 2025/0037; Y10T 29/49826; Y10T 29/49885; Y10T 29/49888; Y10T 29/4987; Y10T 29/49924; Y10T 29/49904; A61H 25/0026; B29C 53/65; B29C 53/821; B29L 2031/7542
See application file for complete search history.

(56) References Cited

U.S. PATENT DOCUMENTS 4,789,768 A * 12/1988 Tobita et al. ............... 219/78.01
6,030,371 A    2/2000 Pursley
(Continued)

FOREIGN PATENT DOCUMENTS

| WO | WO 02/083229 | 10/2002 |
| WO | WO 2004/064891 | 8/2004 |
| WO | WO 2007/121005 | 10/2007 |

OTHER PUBLICATIONS

International Search Report and Written Opinion received in Patent Cooperation Treaty Application No. PCT/US2012/059920, dated Mar. 29, 2013, 12 pages.
(Continued)

*Primary Examiner* — John C Hong
(74) *Attorney, Agent, or Firm* — Haynes and Boone, LLP

(57) ABSTRACT

The present disclosure relates generally to medical tubing and methods of manufacturing medical tubing. In particular, the present disclosure relates to medical catheters and methods of manufacturing medical catheters, including rapid exchange catheters. In some embodiments, catheters of the present disclosure have varying stiffness or rigidity along their length. In some embodiments, catheters of the present disclosure have a guiding portion with a different color than a main body portion. In some embodiments, catheters of the present disclosure have wrapped filaments imbedded therein to provide structural integrity and desired handling characteristics for the catheter. Additional aspects of the present disclosure are apparent from the detailed description.

10 Claims, 23 Drawing Sheets

(52) U.S. Cl.
CPC ..... *Y10T 29/49888* (2015.01); *Y10T 29/49904* (2015.01); *Y10T 29/49924* (2015.01)

(56) References Cited

U.S. PATENT DOCUMENTS

| | | | |
|---|---|---|---|
| 6,961,809 B2* | 11/2005 | Krishnan et al. | 711/108 |
| 2005/0059957 A1 | 3/2005 | Campbell et al. | |
| 2006/0020256 A1 | 1/2006 | Bell et al. | |
| 2007/0106211 A1 | 5/2007 | Provost-Tine et al. | |
| 2007/0249896 A1 | 10/2007 | Goldfarb et al. | |
| 2008/0306465 A1 | 12/2008 | Bailey et al. | |
| 2010/0168642 A1 | 7/2010 | Appling et al. | |
| 2010/0191165 A1 | 7/2010 | Appling et al. | |

OTHER PUBLICATIONS

European Patent Office, "European Office Action," for Application No. 12839934.2, mailed on Mar. 26, 2015, 7 pages.

* cited by examiner

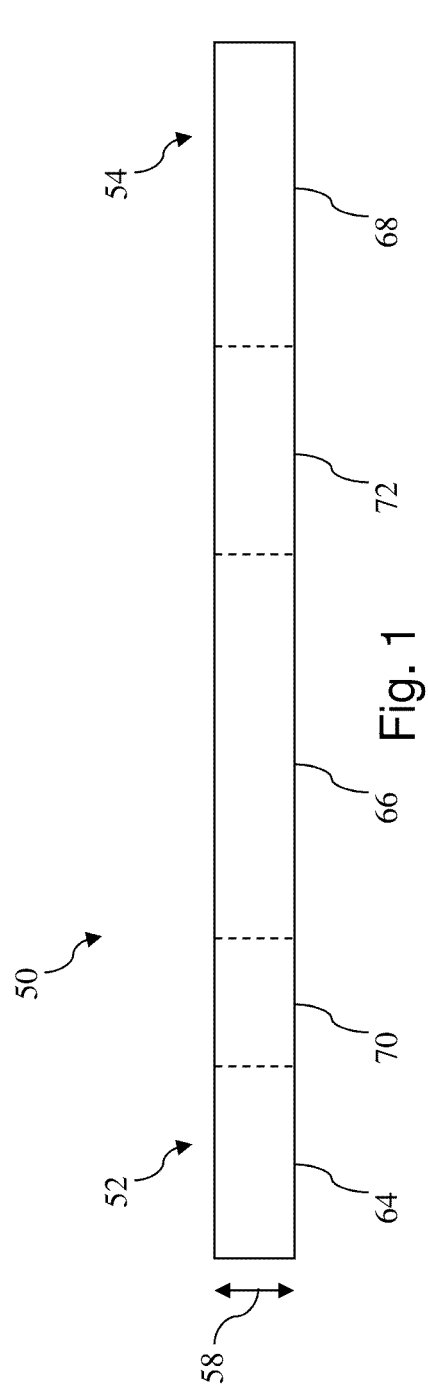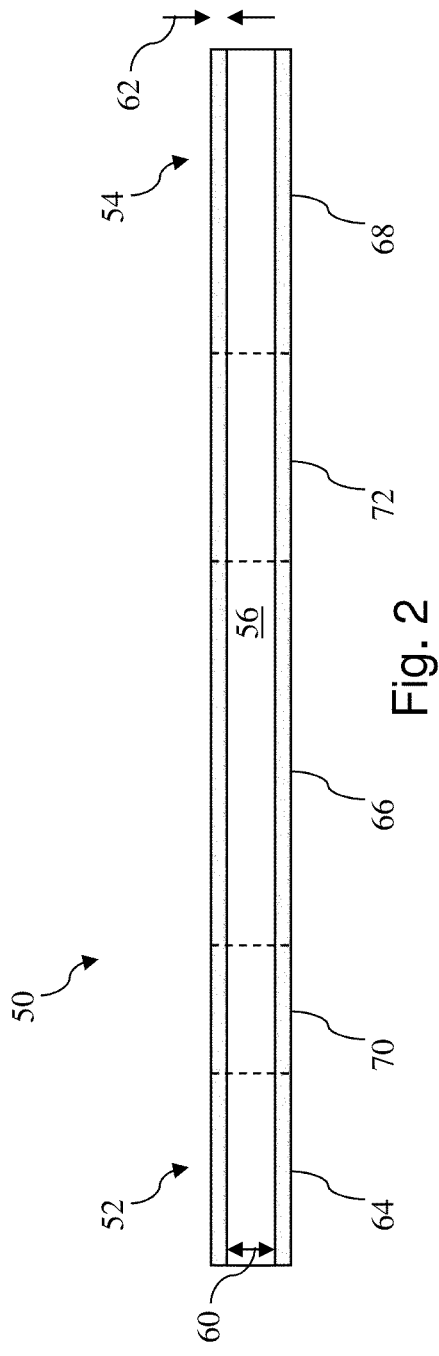

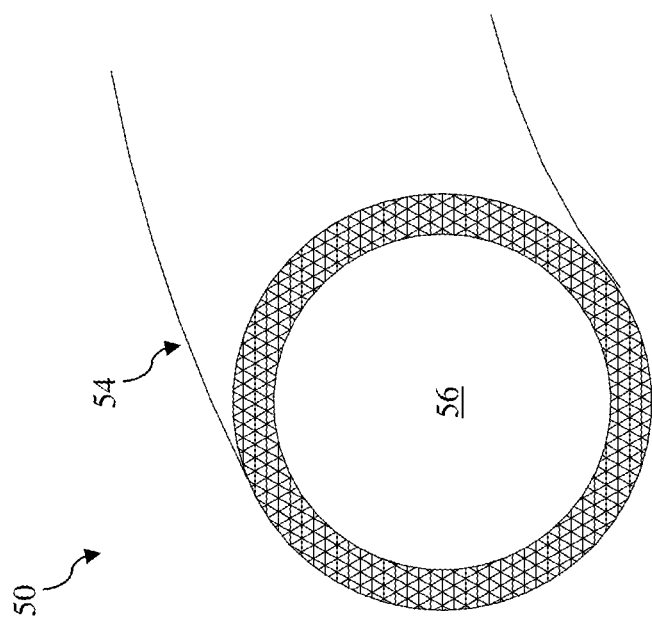

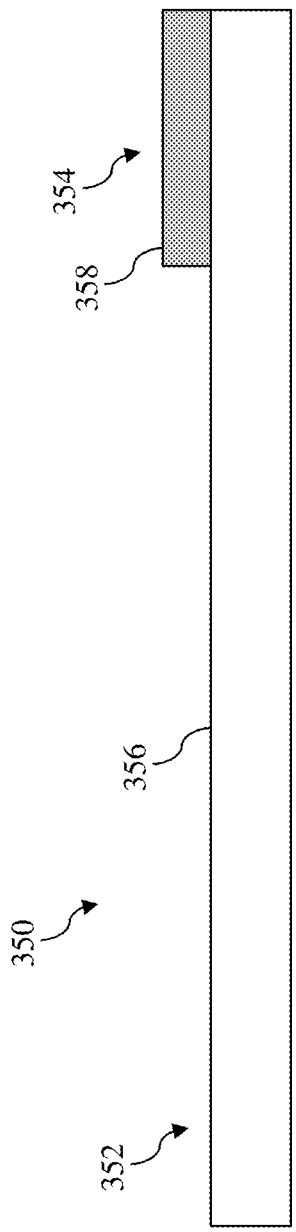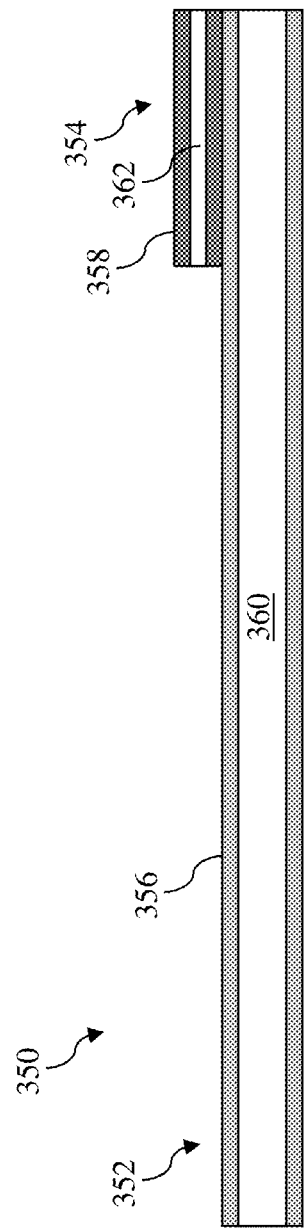

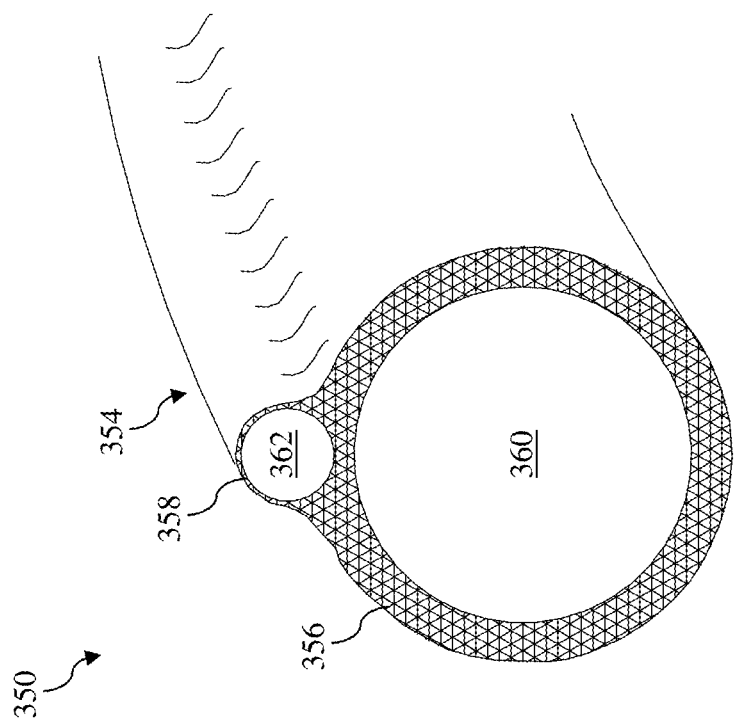

MEDICAL TUBING AND ASSOCIATED DEVICES, SYSTEMS, AND METHODS

CROSS-REFERENCE TO RELATED APPLICATIONS

This application is a non-provisional patent application that claims priority to and the benefit of U.S. Provisional Patent Application No. 61/547,661, filed Oct. 14, 2011, titled "MEDICAL TUBING AND ASSOCIATED DEVICES, SYSTEMS, AND METHODS," which is hereby incorporated by reference in its entirety.

TECHNICAL FIELD

The present disclosure relates generally to medical tubing and methods of manufacturing medical tubing. In particular, the present disclosure relates to medical catheters and methods of manufacturing medical catheters.

BACKGROUND

Medical tubing and catheters are widely employed for a variety of treatment and diagnostic procedures involving, for example, the administration of fluid medications and devices into a patient and the removal of fluids from the patient. In the present disclosure, the terms "catheter" and "medical tubing" will be used interchangeably to refer to an elongated structure having a lumen extending therethrough suitable for medical uses.

The particular use for which the medical tubing is designed requires the tubing to have certain physical characteristics that can vary between uses. Further, different portions of a single catheter are often required to have different physical properties to achieve the desired functionality. For example, a catheter must be sufficiently stiff or rigid to enable its insertion and movement through narrow body orifices and channels and, in some applications, must also be able to withstand a high bursting pressure. On the other hand, a catheter must be sufficiently soft and flexible so that it may readily conform to body shapes so as not to cause injury to the interior wall of a patient's vessel as it is advanced. In addition, a catheter must be of sufficient mechanical strength to resist tearing during normal use, such as when the catheter is removed against tissue resistance.

Accordingly, there remains a need for medical tubing and methods of manufacturing medical tubing that address shortcomings of the previous devices and methods.

SUMMARY

Embodiments of the present disclosure are directed to medical tubing and associated devices, systems, and methods. In some embodiments, the present disclosure is directed to medical catheters, including rapid-exchange catheters.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 1 is a diagrammatic side view of a catheter according to an embodiment of the present disclosure.

FIG. 2 is a diagrammatic cross-sectional side view of the catheter of FIG. 1.

FIG. 3 is a diagrammatic perspective end view of the catheter of FIGS. 1 and 2.

FIG. 20 is a diagrammatic side view of a catheter according to another embodiment of the present disclosure.

FIG. 21 is a diagrammatic cross-sectional side view of the catheter of FIG. 20.

FIG. 22 is a diagrammatic perspective end view of the catheter of FIGS. 20 and 21.

DETAILED DESCRIPTION

Figure 4:
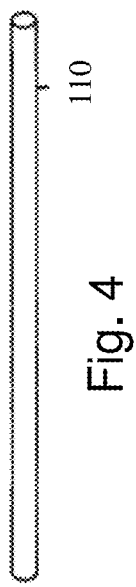
FIG. 4 is a diagrammatic perspective view of mandrel utilized to manufacture a catheter according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Referring initially to FIGS. 1-3, shown therein is a catheter 50 according to an embodiment of the present disclosure. In that regard, FIG. 1 is a diagrammatic side view of a catheter 50; FIG. 2 is a diagrammatic cross-sectional side view of the catheter; and FIG. 3 is a diagrammatic perspective end view of the catheter. As shown in FIGS. 1 and 2, the catheter 50 includes a proximal portion 52 and an opposing distal portion 54. A lumen 56 extends along the length of the catheter between the proximal portion 52 and the distal portion 54. The catheter 50 has an outer diameter 58 and an inner diameter or lumen diameter 60. As a result, the catheter 50 has a wall thickness 62. In general, the catheter 50 is sized and shaped for use within the lumen of a vessel, including both medical and non-medical applications. As will be understood by those skilled in the art, the devices and techniques described herein are suitable for catheters having a wide range of sizes. As a result, the outer diameter 58, inner diameter 60, and wall thickness 62 are not limited to any particular sizes. However, some embodiments of the present disclosure are particularly suited for use in the context of human vessels, including vasculature, and are sized and shaped accordingly. In that regard, in some embodiments the outer diameter 58 is between about 0.014" and about 1.000", the inner diameter is between about 0.011" and about 0.995", and the thickness 62 is between about 0.005" and about 0.900". Further, in some instances, one or more of the outer diameter 58, inner diameter 60, and thickness 62 varies along the length of the catheter 50.

As shown in FIG. 1, the catheter 50 has a varying stiffness or rigidity along its length. In that regard, the catheter 50 is shown as having a section 64 having a first stiffness, a section 66 having a second stiffness different than the first stiffness, and a section 68 having a third stiffness different than the second stiffness. In the illustrated embodiment, the catheter 50 has a transition zone 70 between section 64 and section 66 and a transition zone 72 between section 66 and section 68. In some instances, the stiffness or rigidity of the different sections is adjusted by changing the material (or blend of materials) utilized to form each section. In that regard, by adjusting the hardness of the material utilized to form each section, the resulting stiffness or rigidity of the section can also be controlled. While a wide range of material hardness combinations may be utilized depending on the intended use of the catheter, in some particular vasculature medical applications, section 64 has a hardness of between about 60 and about 80 Shore D, section 66 has a hardness between about 45 and about 65 Shore D, and section 68 has a hardness between about 25 and about 45 Shore D. However, material hardness well outside these ranges is utilized in other applications, including other medical applications.

The manufacturing techniques discussed below allow the catheter 50 to be manufactured in a manner that allows precise control over the stiffness or rigidity of the catheter along its length such that the length of each section 64, 66, and 68, the length of each zone 70 and 72, and the rate of transition between the different rigidities within each zone 70 and 72 can be controlled. For example, in some instances the transition zone has a linear progression between two sections having different rigidities. In general, the longer the transition zone is, the smoother the transition between the different rigidities will be and the less likely the transition will have a negative effect on catheter performance. Accordingly, in some instances the length of the transition zones is between about 10 mm and about 200 mm. However, in other instances, the transition zones 70 and 72 are omitted or have a nominal length (e.g., less than 2 mm) along the longitudinal axis of the catheter. It is understood that while catheter 50 has been described as having three sections and two transition zones between those sections, no limitation is intended thereby as catheters according to the present disclosure may have any number of sections of varying stiffness and any number of transitions (or lack of transitions) therebetween.

Techniques for manufacturing catheter 50 will now be described. In some instances, embodiments of the present disclosure include one or more structural features and/or steps of manufacturing as described in U.S. Pat. No. 6,030,371 filed on Aug. 22, 1997, U.S. Pat. No. 7,445,684 filed on Dec. 11, 2003, U.S. Pat. No. 7,695,753 filed on Oct. 27, 2005, U.S. Pat. No. 7,776,380 filed on Sep. 22, 2005, and/or U.S. patent application Ser. No. 11/261,544 filed on Oct. 27, 2005, each of which is hereby incorporated by reference in its entirety.

Figure 5:
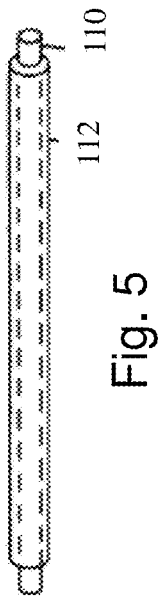
FIG. 5 is a diagrammatic perspective view similar to that of FIG. 4, but illustrating a liner positioned over the mandrel according to an embodiment of the present disclosure.

Referring now to FIGS. 4-19 various aspects of methods of manufacturing a catheter will be described. A core mandrel 110 is provided, as shown in FIG. 4, over which the catheter will be constructed. In that regard, the core mandrel 110 is a wire having a circular cross-section in some instances. In that regard, the cross-sectional diameter of the core mandrel 110 is selected to be equal to or slightly less than the desired inner diameter of the resulting catheter. In some embodiments, a catheter liner 112 is placed over the mandrel 110, as shown in FIG. 5. The liner 112 can be formed of a variety of different materials but is generally less than 20% of the intended wall thickness. For example, a liner having a wall thickness between about 0.0005" and about 0.200" is utilized in some instances. Further, in some embodiments the liner is formed of polytetrafluoroethylene (e.g., Teflon®) or other suitable material that provides a lubricious and/or smooth surface that can be used to define the inner lumen of the catheter. Alternatively, the process of the present disclosure can be performed without a liner, whereby the techniques discussed below are applied directly over the mandrel 10.

Figure 6:
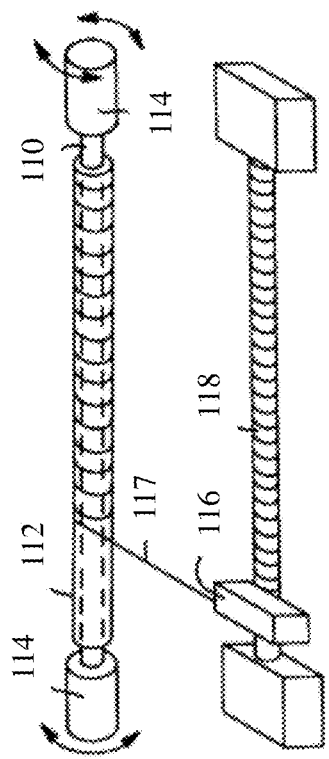
FIG. 6 is diagrammatic perspective view of the mandrel and liner of FIG. 4 shown with a winding mechanism and filament according to an embodiment of the present disclosure.

As shown in FIG. 6, in some embodiments one or more reinforcement filaments 117 are applied over the liner 112. In some embodiments, the filament 117 is a filament having a circular, rectangular, square, D-shaped, and/or other cross-sectional profile. Generally, the filament 117 is formed of any suitable material including without limitation metals (e.g., stainless steel, nitinol, etc.) and polymers (e.g., polyethylene, etc.). In one implementation of this technique, the mandrel 110 and liner 112 are loaded into rotating chucks 114. A filament winding mechanism 116 is then traversed longitudinally along the length of the mandrel 110 to apply a reinforcement filament 117 over the mandrel at a winding angle range of 0 to 90 degrees relative to the longitudinal axis of the catheter. In some embodiments, the winding mechanism is translated using a screw carrier 118. The winding angle of the filament 117 can be varied over the length of the catheter by controlling the rotation speed of the mandrel 110 and the movement of the filament winding mechanism 116 along the support 118 to account for portions of the catheter that require great circumferential rigidity or kink resistance and other portions that require low rigidity. Further, as discussed below, multiple layers of filaments having different winding angles or other characteristics can be utilized to control the physical characteristics and resulting performance of the catheter.

Although FIG. 6 shows a process in which the core member 112 is rotated about its axis and the filament source 116 is moved parallel to the core member 112, it will be understood by those skilled in the art that other methods of moving the core member 112 relative to the filament source 116 are also possible. For example, the core member 112 can be held stationary while the filament source 116 orbits around the core member 112 and also moves along a length of the core member 112 to wind the filament 117 on the core member 112. For another example, the filament source 116 can be held stationary while the core member 112 rotates about its axis and also moves in an axial direction. It is understood that each of these process variations and others can be used to accomplish the desired relative movement between the core member 112 and the filament source 116.

Figure 7:
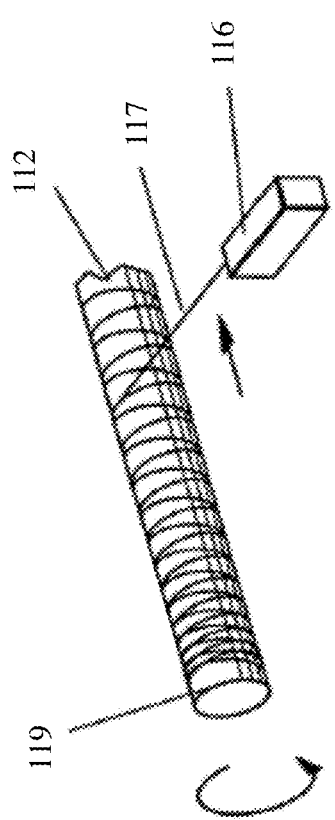
FIG. 7 is a diagrammatic perspective view illustrating a technique of winding a filament around a core for forming a catheter according to an embodiment of the present disclosure.
Figure 8:
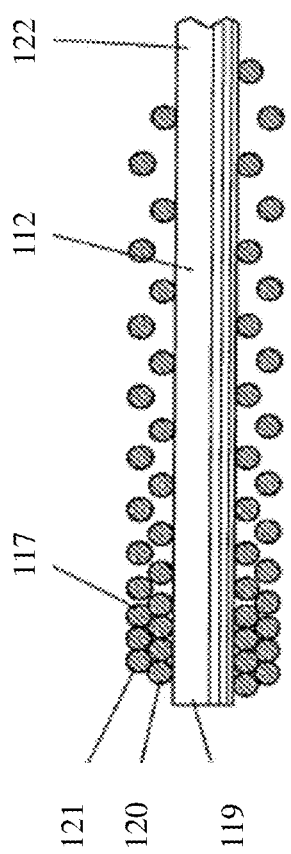
FIG. 8 is a diagrammatic cross-sectional side view of a portion of the core and filament according to the winding technique of FIG. 7.

Once the filament winding 117 reaches the distal end 119 of the core member 12 (the left side of FIG. 6), a first pass 120 of the filament winding 117 over the core member 112 is completed (as shown in FIG. 8). In that regard, the filament winding 117 can have a variable pitch in which the turns of the filament 117 become closer together near the distal end 119 of the liner 12. Alternatively, the filament winding 117 can have a constant pitch in which the turns of the winding are evenly spaced over the entire length of the liner 12. When the first pass 120 is completed, the filament source 116 reverses its direction of axial movement while the core 110 and liner 112 continue to rotate relative to the filament source 16. A second pass 121 of the filament winding 117 is then applied over the liner 112 (and over the first pass 120 of the filament winding 117) as the filament source 116 moves back toward a proximal end 122 of the liner 112. As a result, the filament winding 117 is continuous from its initial anchor at the proximal end 122, to the end of the first pass 120 at the distal end 119 of the liner 112, and then back to the end of the second pass 121 at the proximal end 122. As shown in FIGS. 7 and 8, the second pass 121 of the winding 117 can be applied with a variable pitch similar to the first pass 120. Also, the filament 117 is shown as having a circular cross-sectional profile in the embodiment of FIG. 8.

Figure 9:
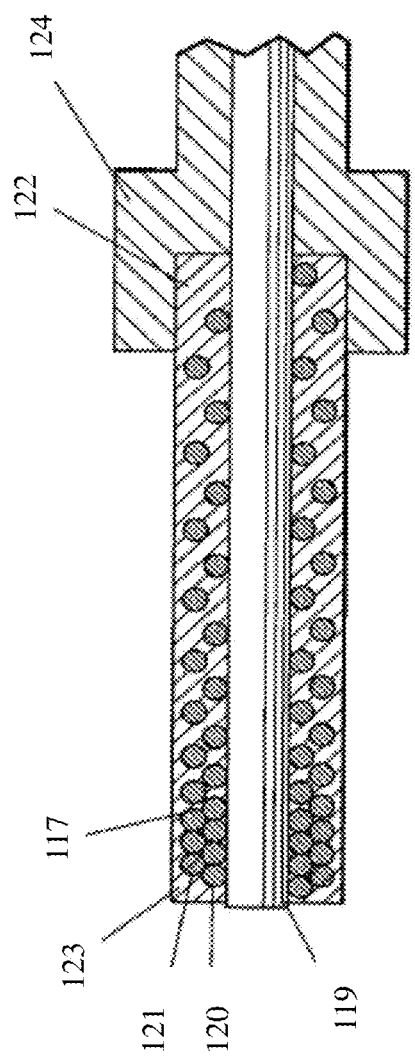
FIG. 9 is a diagrammatic cross-sectional side view of the catheter formed by the technique of FIGS. 7 and 8.

In some embodiments, the first and second passes 120, 121 of the filament winding 117 together form a first winding layer of the catheter 10. A coating 123 is applied over the first winding layer as shown in FIG. 9. The coating 123 can be formed by applying a polymer material in a particulate perform over an outer surface of the liner 112 and the winding layer. A suitable process for applying the plastic coating in this manner is disclosed, for example, in U.S. Pat. No. 6,030,371, which is incorporated herein by reference. Alternatively, the coating 123 can be applied by laminating a plastic tube over an outer surface of the liner 112 (or mandrel 110 directly) and the winding layer, by extruding the plastic material over the winding layer, or by using electrostatic forces to apply the coating material as a molecular strand using a nanospinning process. After the coating 123 is applied, the proximal end 122 of the catheter is anchored in a suitable hub 124.

Figure 10:
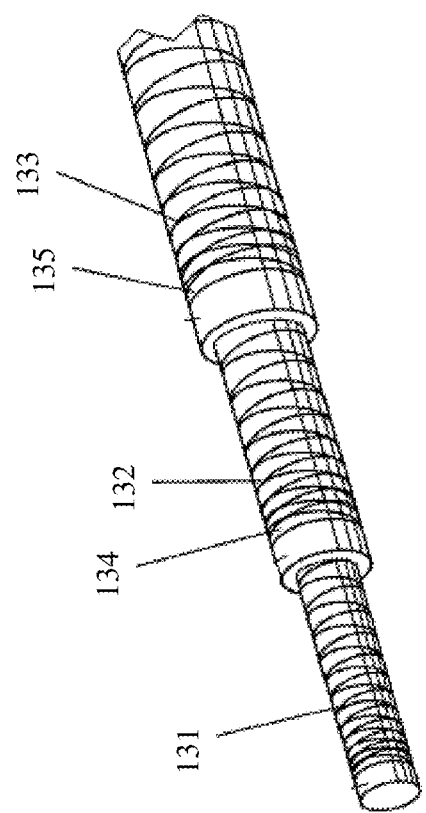
FIG. 10 is a diagrammatic perspective view illustrating a technique of winding a filament around a core for forming a catheter according to another embodiment of the present disclosure.
Figure 11:
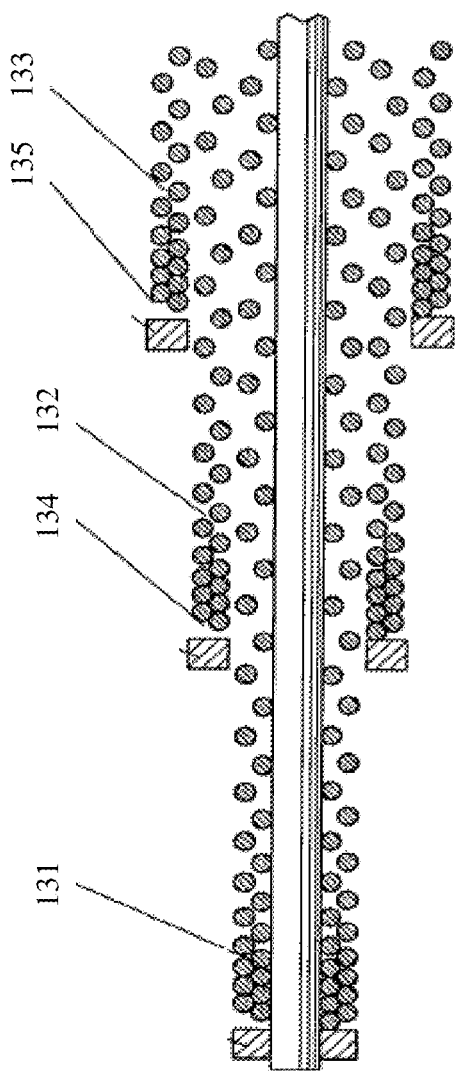
FIG. 11 is a diagrammatic cross-sectional side view of a portion of the core and filament according to the winding technique of FIG. 10.

As shown in FIGS. 10 and 11, a catheter having multiple reinforcement layers 131, 132, 133 can be formed by repeating the process described above. Specifically, the first layer 131 of the catheter can be formed using the same process used to forming the passes 120, 121 in FIGS. 8 and 9. The additional fibrous layers 132, 133 can be applied over the first fibrous layer 131 to impart different properties along the length of the catheter. Each additional winding layer 132, 133 can be formed in a manner similar to the first layer 131. Specifically, the filament for the first additional layer 132 is anchored in the proximal end, and then the filament is wound over the first fibrous layer 131 as the filament source is moved axially along the core member from the proximal end to a distal position and then back to the proximal end.

In some embodiments, the distal end 134 of the first additional layer 132 is an intermediate point along the catheter between the proximal and distal ends, as shown in FIGS. 10 and 11. The second additional layer 133 can be formed in a similar manner to the first additional layer 132. The distal end 135 of the second additional layer 133 is at another intermediate point along the catheter in some instances. As shown in FIGS. 10 and 11, the additional layers 132, 133 can be progressively shorter than the first layer 131 so that the catheter has a tapering profile and variable properties along its length. Alternatively, two or more of the layers 131, 132, and 133 have the same length in other embodiments. Further, in some embodiments, while the layers 131, 132, and/or 133 have different lengths the overall outer catheter diameter remains constant along the length of the device. The pitch of the windings in each layer 131, 132, 133 can be varied as shown in FIGS. 10 and 11, or the pitch can be constant (not shown) so that the windings of a particular layer are spaced uniformly over a length of the catheter. A plastic coating can be applied over all of the layers 131, 132, and 133 simultaneously, or the coating can be applied over each of the layers separately before the next layer is formed.

Figure 12:
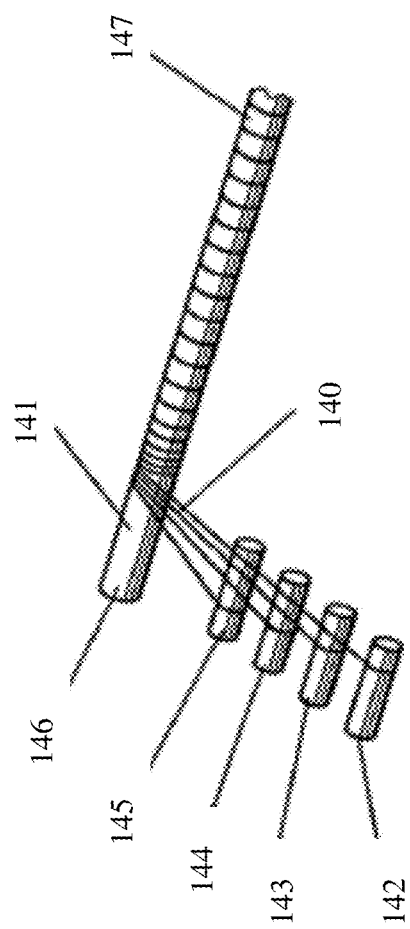
FIG. 12 is a diagrammatic perspective view illustrating a technique of winding a plurality of filaments around a core for forming a catheter according to an embodiment of the present disclosure.

In another variation of the present invention, a group of filaments 140 are wound on the core member 141 simultaneously. As shown in FIG. 12, the group of filaments 140 can be supplied from a plurality of filament sources 142-145 (e.g., bobbins or spools). Generally, the group of filaments 140 can consist of any number of filaments, including two or more. In some instances, the group of filaments consists of between 2 and 15 filaments. In the illustrated embodiment the group of filaments consists of 4 filaments. The filament sources 142-

145 are moved in a controlled manner relative to the core member 141 so that windings apply either a constant or a variable pitch over a length of the core member 141. For example, the group of filaments 140 can be wound with a variable pitch such that a filament group spacing at a distal end 146 of the core member 141 is narrower than a filament group spacing at a proximal end 147 of the core member 141, as shown in FIG. 12. The filament sources 142-145 can also be moved relative to each other to vary the spacing between the filaments within the group 140 as the winding progresses over a length of the catheter. For example, the filament spacing between the filaments within the group 140 at a distal end 146 of the core member 141 can be made narrower than the filament spacing at a proximal end 147 thereof. In still another embodiment, the group of filaments 140 can be wound with a variable pitch and a variable spacing between the filaments within the filament group 140.

Figure 13:
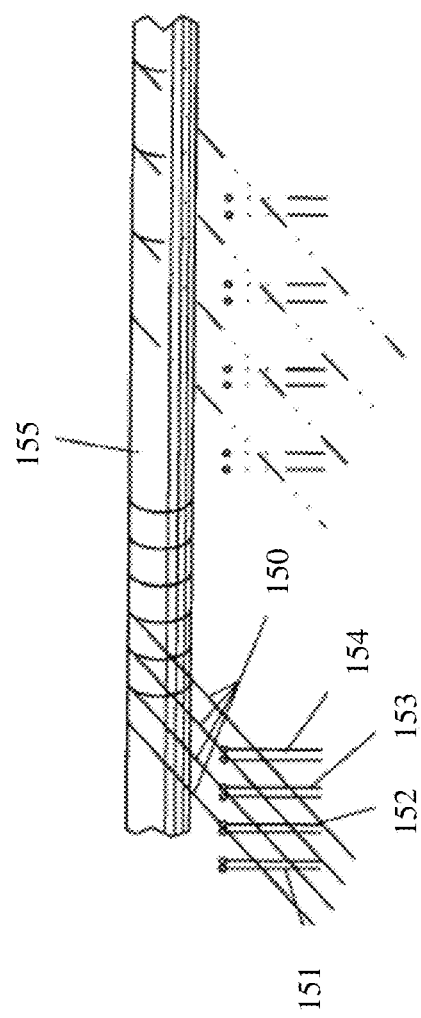
FIG. 13 is a diagrammatic perspective view illustrating a technique of winding a plurality of filaments around a core for forming a catheter according to another embodiment of the present disclosure.

As shown in FIG. 13, a plurality of wire guides 151-154 can be used to control the filament spacing within a group of filaments 150. In this case, the spacing between the wire guides 151-154 can be varied as the winding proceeds along a length of the core member 155 to change the filament spacing within the filament group 150. The use of wire guides 151-154 helps eliminate slight fluctuations in spacing that can occur when the filaments are simply fed off of a spool or bobbin and directly onto the core member 155.

Figure 14:
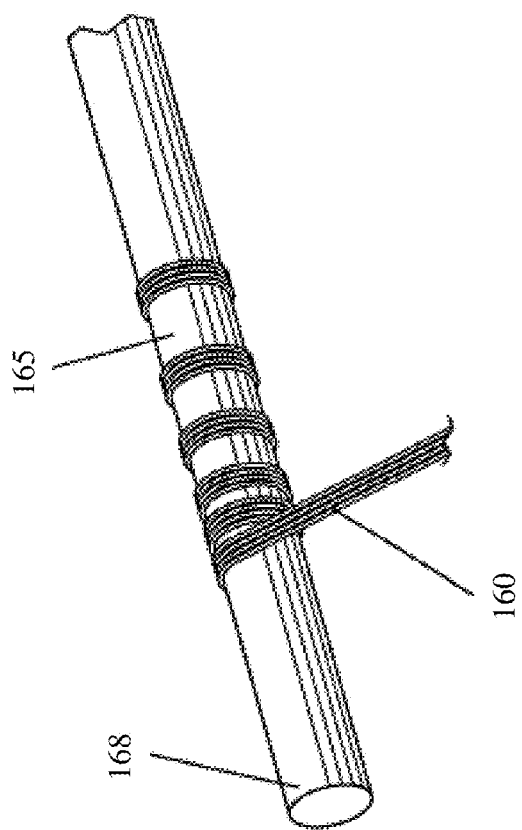
FIG. 14 is a diagrammatic perspective view illustrating a technique of winding a plurality of filaments around a core for forming a catheter according to yet another embodiment of the present disclosure.
Figure 15:
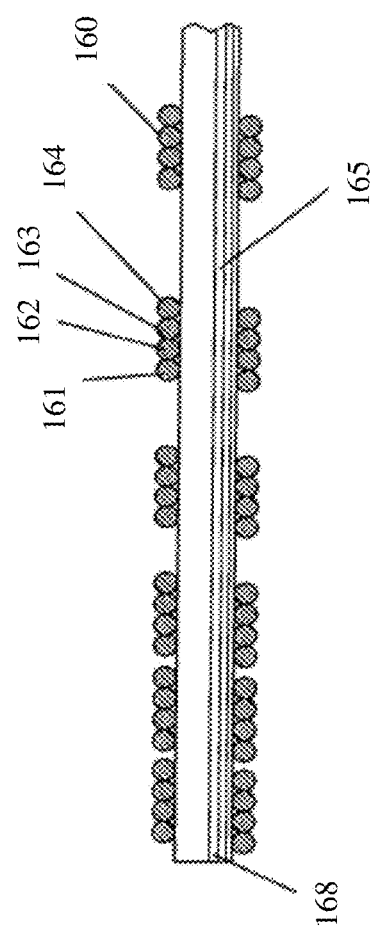
FIG. 15 is a diagrammatic cross-sectional side view of a portion of the core and plurality of filaments according to the winding technique of FIG. 14.
Figure 16:
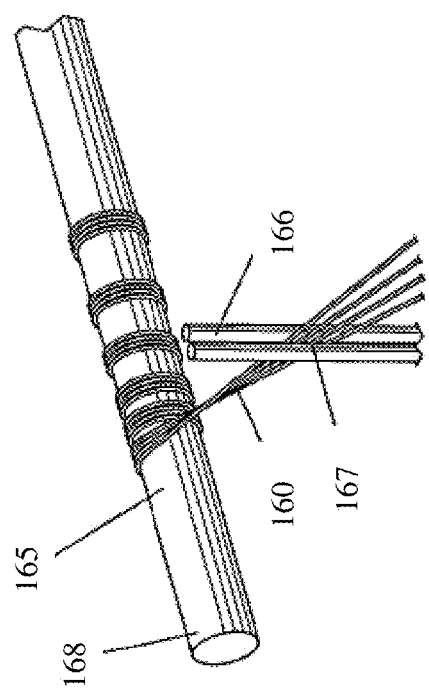
FIG. 16 is a diagrammatic perspective view illustrating a technique of winding a plurality of filaments around a core for forming a catheter according to another embodiment of the present disclosure.

Referring now to FIGS. 14-16, shown therein is an additional embodiment in which a group 160 of filaments 161-164 is wound onto the core member 165 in a close, side-by-side arrangement. The closely packed group 160 is formed using a guide assembly 166, depicted in FIG. 16, which has a filament engaging surface 167 that lies in a plane generally perpendicular to a longitudinal axis of the core member 165. In this embodiment, the guide assembly 166 functions as the filament source. As the group 160 of filaments 161-64 pass through the guide assembly 166, the filaments 161-164 are arranged in a common plane which is approximately perpendicular to a plane containing the filaments 161-164 as they first engage an outer surface of the core member 165. For example, if the axis of rotation of the core member 165 is horizontal, the filament engaging surface 167 of the guide assembly 166 can extend along a vertical line.

The guide assembly 166 arranged in this manner causes the filaments 161-164 within the group 160 of filaments to be positioned side-by-side and packed tightly against one another as the group 160 of filaments are wound onto the core member 165. The pitch of the group 160 of filaments being wound onto the core member 165 can be varied by varying a rotation speed of the core member 165 and/or a translation speed of the guide assembly 166 as the filament source, in the manner described above. The guide assembly 166 can be used to apply a group 160 of filament windings in two continuous passes to form a first fibrous layer over the outer surface of the core member 165. In this case, all of the ends of the filaments 161-164 can be anchored in the proximal end of the catheter, and the filaments 161-164 will be continuous at the distal end 168 of the catheter to avoid fraying and improving the performance of the catheter. Alternatively, the guide assembly and the other methods described herein for applying a group of filaments simultaneously can be used to form a fibrous layer in the catheter with a single pass over the core member and the distal ends of the filaments anchored at the distal end of the catheter.

Figure 17:
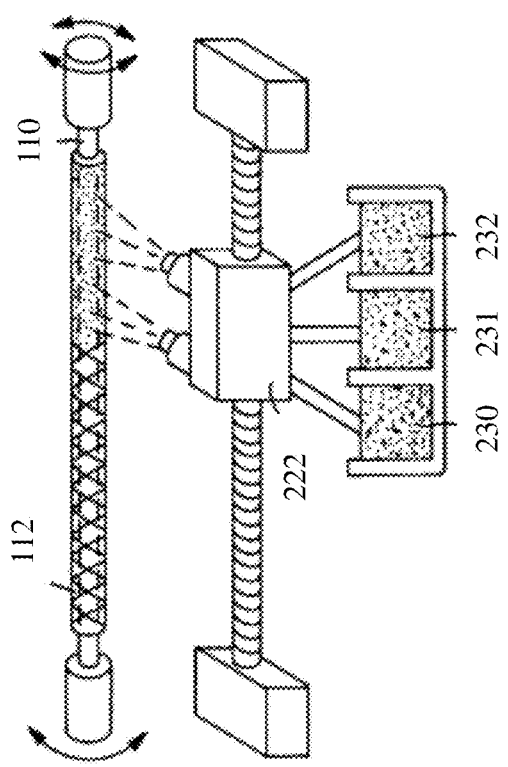
FIG. 17 is a diagrammatic perspective view of an arrangement for manufacturing a catheter according to an embodiment of the present disclosure.

Referring now to FIG. 17, at either the same time or after winding the filament(s), a spray head 222 also traverses the mandrel/liner. In some embodiments, the spray head 222 applies an atomized spray (e.g., a molten polymer in an inert gas stream) that thermally fuses to the substrate it impinges upon (i.e., the mandrel 110, the liner 112, or the reinforcement filament 117). The substrate is preheated in some instances to ensure complete fusion of the sprayed polymer to the substrate. This preheating can be accomplished with infrared, hot air, or resistance heating of the core mandrel 110 or other suitable means.

Figure 18:
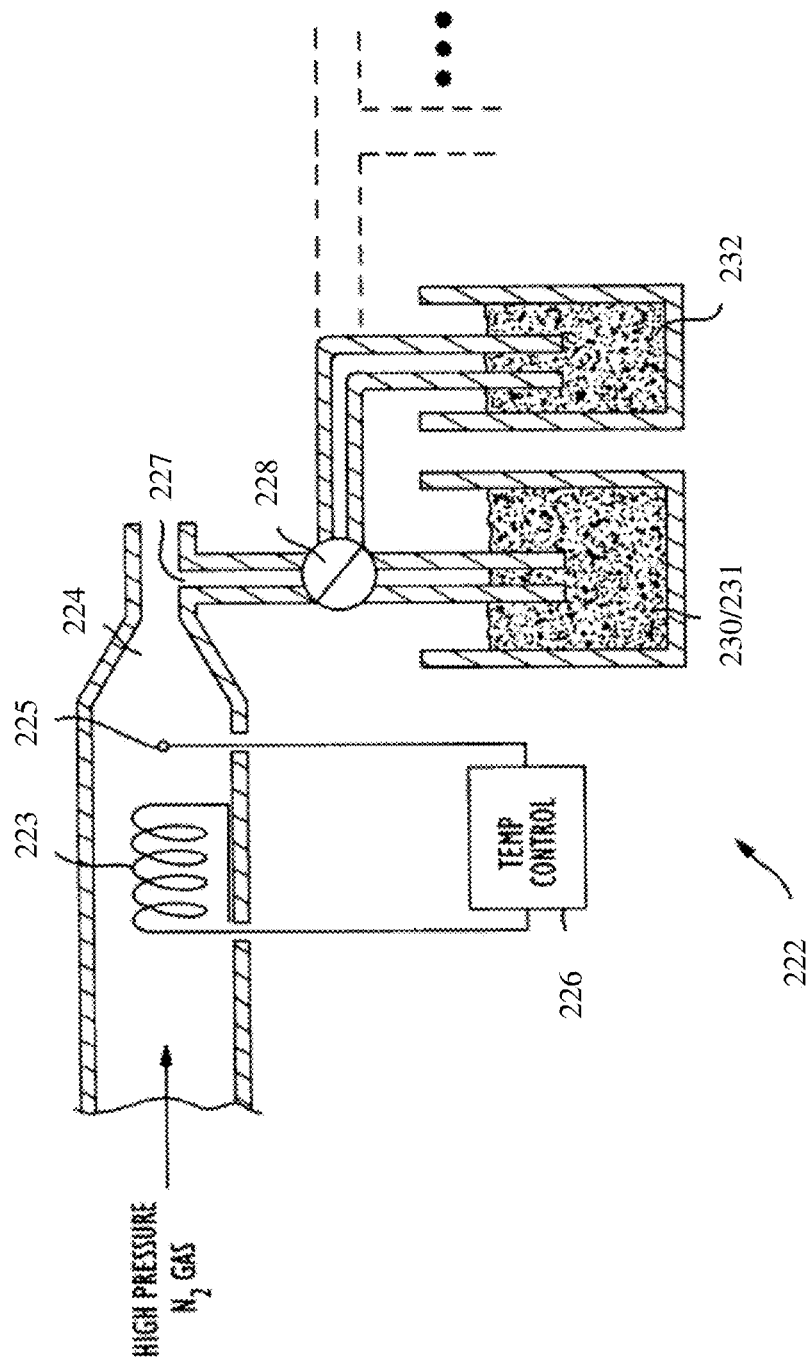
FIG. 18 is a diagrammatic, schematic cross-sectional side view of a system configured to apply polymer to a core according to an embodiment of the present disclosure.

The atomized spray head 222 according to a first embodiment of the present invention is shown in detail in FIG. 18. As shown, high pressure gas, such as nitrogen, is piped past a heater 223 and through a venturi 224 of the spray head 222. A temperature sensor 225, such as a thermocouple, is provided in the flow within the spray head 222 to monitor the gas temperature. A temperature controller 226 is used to maintain the desired temperature of the gas flowing through the venturi 224. The throat 227 of the venturi 224 is connected to a digitally controlled metering valve 228, which in turn is connected to multiple containers 230, 231, etc. of plastic powders or the like having varying hardness, color, or other property and, in some embodiments, also to a container 232 of opacifying powder such as tungsten.

While the mandrel/liner 110, 112 is spinning, the atomizing spray head 222 traverses along a path parallel to the axis of the rotating mandrel/liner. As it traverses this path, the metering valve 228 is set to apply varying amounts of the powders within each of the containers based on the desired properties of the catheter. For example, in one embodiment, initially only the harder polymer (e.g., from container 230) is applied at what will be the proximal end of the catheter. As the head 222 traverses the mandrel/liner 110, 112, the metering valve 228 is controlled such that it ports to the harder polymer to a lesser degree and to the softer polymer (e.g., from the container 231) to a higher degree until finally only the softest polymer is applied at the distal tip of the catheter, which will serve as the soft tip of the catheter-body. Similar techniques can be used with any number of different containers of powders to create a catheter having any number of sections with varying polymeric properties (in addition to any variances created by any applied winding layer(s)).

In a similar fashion, opacifying powder can be selectively applied from the container 232. A single layer of polymer can be applied as the filaments are placed. The single layer of polymer can be followed by a layer of opacifier and finally a finish layer of polymer. A benefit of applying opacifier in this manner is that the movement of the head 222 can be paused momentarily to apply circumferential rings of high opacifier concentration that can serve as markers on the catheter when the catheter is used under X-ray. The opacifier powder in this embodiment can be heated to a high enough temperature so that it melts the substrate it impinges upon and thereby adheres to the surface of the substrate until it is overcoated with a finish layer of polymer.

After the catheter is completely coated with polymer from the spray head 222, the catheter is rough-sized by passing a cutter over the surface of the catheter and then polished and/or or shaped with a laser cutter that does not contact the surface of the catheter. The catheter body is then removed from the rotating chucks 114 and is ready for finishing operations, such as curving or hubbing. A laser arrangement 50 for sizing the tubing after the polymer coating is consolidated on the liner/mandrel. As shown, the laser arrangement 50 includes a laser cutter 51 which can be moved along a threaded shaft 52 or the like for movement parallel to the rotating mandrel 10.

Figure 19:
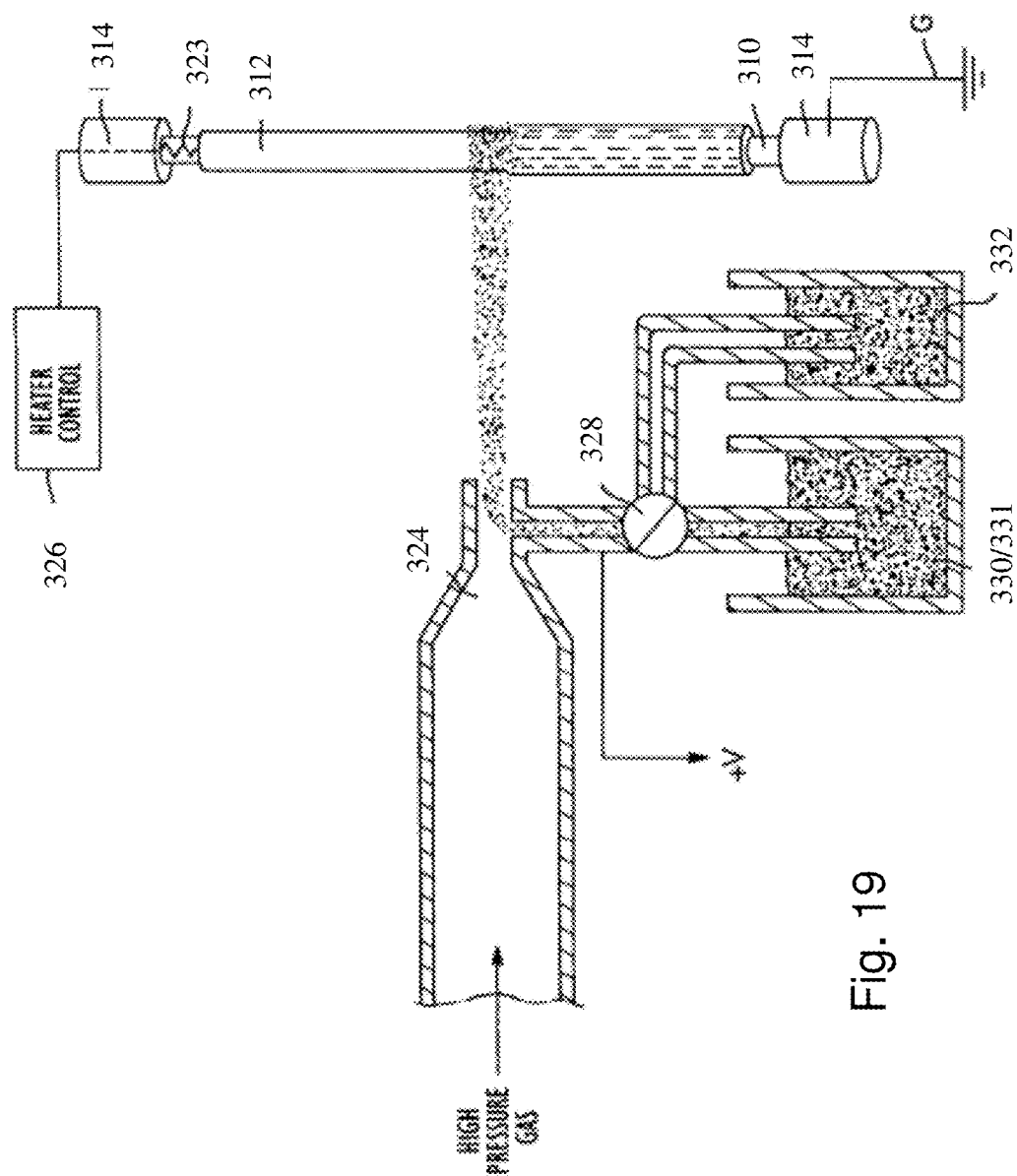
FIG. 19 is a diagrammatic, schematic cross-sectional side view of an arrangement for manufacturing a catheter according to another embodiment of the present disclosure.

Referring now to FIG. 19, another embodiment of the present disclosure will be described. As shown, the catheter manufacturing method according to this embodiment is performed by applying an unmelted polymer powder to a heated mandrel/liner 310, 312. In this embodiment, the mandrel 310 and liner 312 are heated by a heater 323 to above the melting point of the powder material (e.g., above 380 degrees F. for some plastic powders). In some instances, the heater 323 is a resistance heater controlled by a heater controller 326, as shown in FIG. 19. Alternatively, the heater can be an infrared or hot air heater, or other suitable means for heating the mandrel 310 and/or liner 312 to the required temperature for melting the powder material.

The unmelted powder is then sprayed onto the surface of the heated mandrel 310 or liner 312 using the spray head 322. The metering valve 328 operates as described above to selectively dispense powder materials from containers 330, 331, 332, and so on to form a catheter having variable properties (e.g., hardness, opacity, color, etc.) along its length. As shown in FIG. 19, the mandrel 310 is grounded through a ground G, and the powder material is charged through a positive source +V as the unmelted powder is applied, thereby causing the powder to electrostatically cling to the heated mandrel 310 or liner 312 during application. When the powder impinges upon the heated mandrel 310 or liner 312, the powder melts to form a uniform coating over the surface thereof. A series of fine coating layers can be applied over the mandrel 310 or liner 312 by making several passes of the spray head 322 over the length or selected portions of the catheter. The coated mandrel or liner can then be baked or otherwise heated to further consolidate and cure the coating(s) as necessary.

Referring now to FIGS. 20-22, shown therein is a catheter 350 according to another embodiment of the present disclosure. In that regard, FIG. 20 is a diagrammatic side view of a catheter 350; FIG. 2 is a diagrammatic cross-sectional side view of the catheter; and FIG. 3 is a diagrammatic perspective end view of the catheter. As shown in FIGS. 1 and 2, the catheter 350 includes a proximal portion 352 and an opposing distal portion 354. In that regard, the catheter includes a main body 356 and a guiding body 358. The guiding body 358 makes the catheter 350 suitable for use as a rapid-exchange or monorail catheter. In the illustrated embodiment, the guiding body 358 is positioned at the distal end of the catheter 350. In other embodiments, the distal end of the guiding body 358 is spaced from the distal end of the catheter. A lumen 360 extends along the length of the main body 356 between the proximal portion 352 and the distal portion 354. Similarly, a lumen 362 extends through the guiding body 358. The lumen 362 extends parallel to the lumen 360 in the illustrated embodiment. In other embodiments, the lumen 360 extends at an oblique angle with respect to the lumen 360 and/or the longitudinal axis of the main body 356.

In general, the catheter 350 is sized and shaped for use within the lumen of a vessel, including both medical and non-medical applications. As will be understood by those skilled in the art, the devices and techniques described herein are suitable for catheters having a wide range of sizes. As a result, the outer diameter, inner diameter, and wall thicknesses of the main body 356 and guiding body 358 are not limited to any particular sizes. However, some embodiments of the present disclosure are particularly suited for use in the context of human vessels, including vasculature, and are sized and shaped accordingly. For example, in some instances the lumen 362 of the guiding body 358 is sized to receive a guidewire. In some particular instances, the lumen 362 is sized to receive a guidewire having a diameter of 0.018", 0.014", 0.011", or other size. In that regard, it is understood that the lumen 362 will have a diameter slightly larger than the diameter of the guidewire it is to receive. For example, in one embodiment intended to receive a 0.014" guidewire, the lumen 362 has a diameter of 0.017".

As shown in FIGS. 20 and 21, the guiding body 358 is formed of a different colored material than the main body 356. In that regard, the gradient in color difference between the guiding body 358 and the main body 356 of the catheter is sufficient to cause the guiding body and the main body to be easily distinguished from one another. Accordingly, the guiding body 358 and main body 356 may be different shades of the same color (e.g., dark blue vs. light blue, dark green vs. light green, etc.), different colors (e.g., blue vs. yellow, black vs. white, black vs. clear, etc.), and/or combinations thereof (e.g., dark blue vs. light yellow, dark blue vs. clear, etc.). As discussed below, in some instances the main body 356 and the guiding body 358 are formed separately and then joined together using one or more of the techniques described herein. Accordingly, in some instances a particular color pigment is added to the polymer that forms each of the main body 356 and the guiding body 358 and the two components are joined together with the use of a clear or at least translucent material such that the underlying distinguishable colors of the main body 356 and guiding body 358 are visible after the components are joined together. Because virtually any color pigment can be added to the polymer powders used to form the catheters of the present disclosure, any desired color combination of the main body 356 and the guiding body 358 can be obtained. In some embodiments, the guiding body 358 is selected to be a darker color than the main body 356. In that regard, Applicants have found that in instances where the lumen 362 of the guiding body 358 is small (e.g., less than 0.050", less than 0.025", and/or less than 0.017") the darker color makes the guiding body 358 easily identifiable and the lumen 362 is easier to locate and, therefore, easier to insert a guidewire through the lumen.

Figure 23:
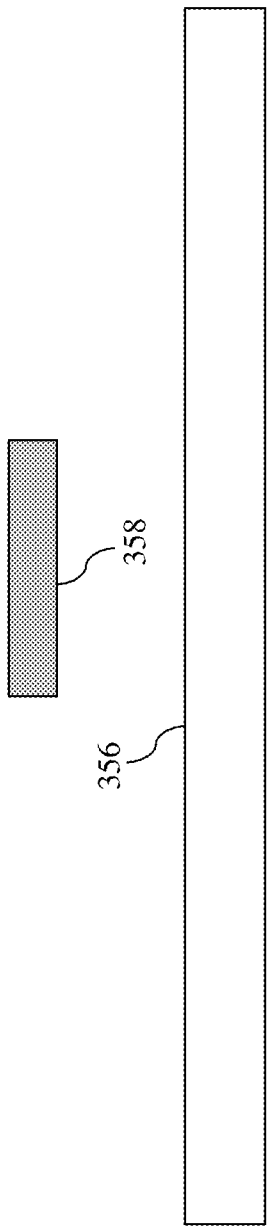
FIG. 23 is a diagrammatic side view of separated components of a catheter according to an embodiment of the present disclosure
Figure 24:
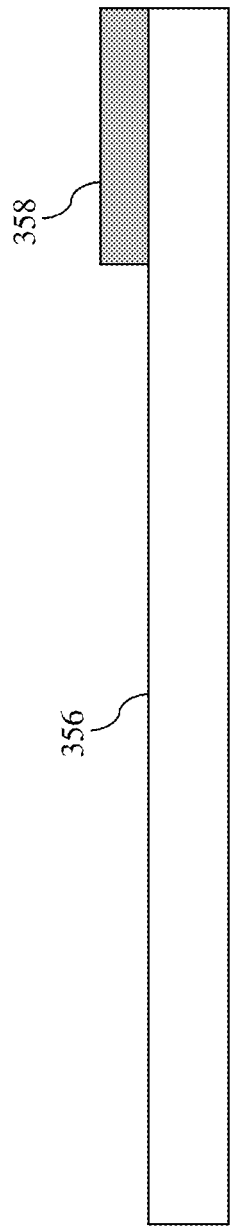
FIG. 24 is a diagrammatic side view of the separate components of FIG. 23 positioned together in preparation for forming the catheter according to an embodiment of the present disclosure.

Referring now to FIGS. 23-29, shown therein are techniques for forming the catheter 350 according to various embodiments of the present disclosure. Referring initially to FIG. 23, the main body 356 and the guiding body 358 are shown separately. In that regard, each of the main body 356 and the guiding body 358 may be formed using one or more of the techniques discussed above for creating a catheter or medical tubing, including spraying a plastic powder around a core (such as a mandrel or liner) and/or embedding one or more filament layers with the catheter. Further, the main body 356 and the guiding body 358 will be formed of contrasting colors as discussed above. As shown in FIG. 24, the guiding body 358 is positioned along the main body 356 such that it can be secured to the main body using one or more of the techniques discussed below. In that regard, the guiding body 358 is typically positioned such that it extends parallel with the main body 356 when secured to the main body, as shown in FIG. 24.

Figure 26:
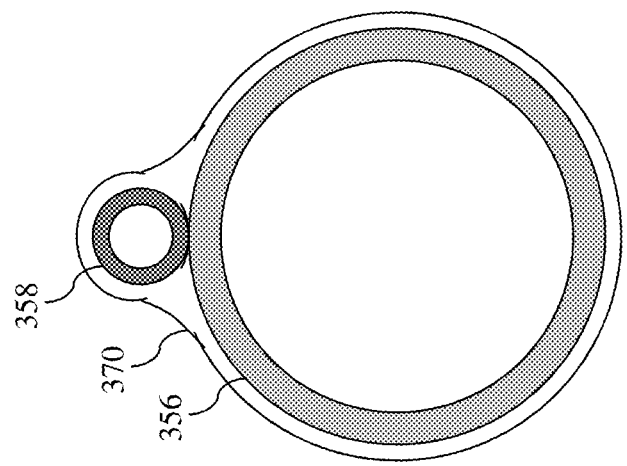
FIG. 26 is a diagrammatic end view similar to that of FIG. 25, but showing the separated components joined together to form the catheter.
Figure 25:
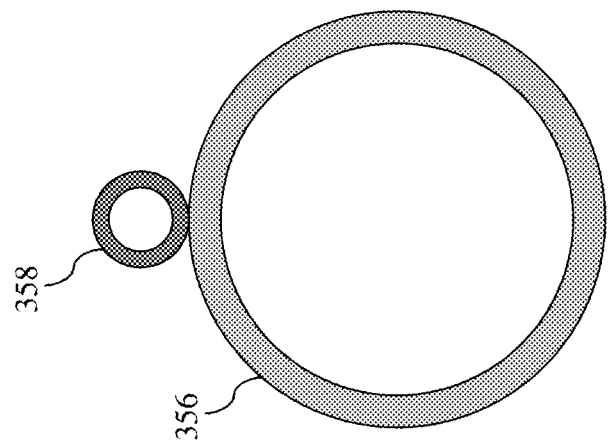
FIG. 25 is a diagrammatic end view of the separate components in the orientation of FIG. 24.

Referring now to FIGS. 25 and 26, shown therein is one technique for securing the guiding body 358 to the main body 356. In that regard, FIG. 25 is a diagrammatic end view of the separate components in the orientation of FIG. 24 (i.e., the guiding body 358 has been positioned along the main body 356 in the desired position to be secured to the main body). In some instances, the main body 356 and guiding body 358 are heated using a heat gun, oven, or other suitable mechanism for heating the components such that at least an outer portion of the main body and guiding body are able to bond with an additional layer of polymer that is sprayed over them. In that regard, the additional layer(s) of polymer may be added using one or more of the techniques described above. FIG. 26 illustrates the main body 356 and guiding body 358 embedded within an additional polymer layer 370. While the main body 356, guiding body 358, and additional layer 370 are shown as having distinct boundaries, this is merely to illustrate the different components that come together to form the catheter, as it is understood that the heating of the guiding body 358 and the main body 356 in combination with application of the additional layer 170 results in a single cohesive unit with bonding between the materials of each of the components. In contrast to previous methods of forming a rapid exchange catheter, this approach avoids the need for using a separate adhesive or glue in an attempt to join a guiding body to the main body that creates risk of the guiding body breaking off of the main body during use. Further, in contrast to previous techniques where the guiding body and the main body were extruded from the same material as a single monolithic component, the techniques of the present application allow the guiding body and the main body to have different properties and, in particular, different colors.

In some instances, the main body 356 and the guiding body 358 are held in place with respect to one another while the additional layer(s) of polymer are added. For example, in some embodiments, mandrels remain positioned within each of the main body 356 and the guiding body 358 and the mandrels are attached to rotating chucks in a similar manner to how mandrel 110 is connected to rotating chucks 114, such that the mandrels and, therefore, the main body and guiding body remain in a fixed orientation with respect to one another.

Figure 27:
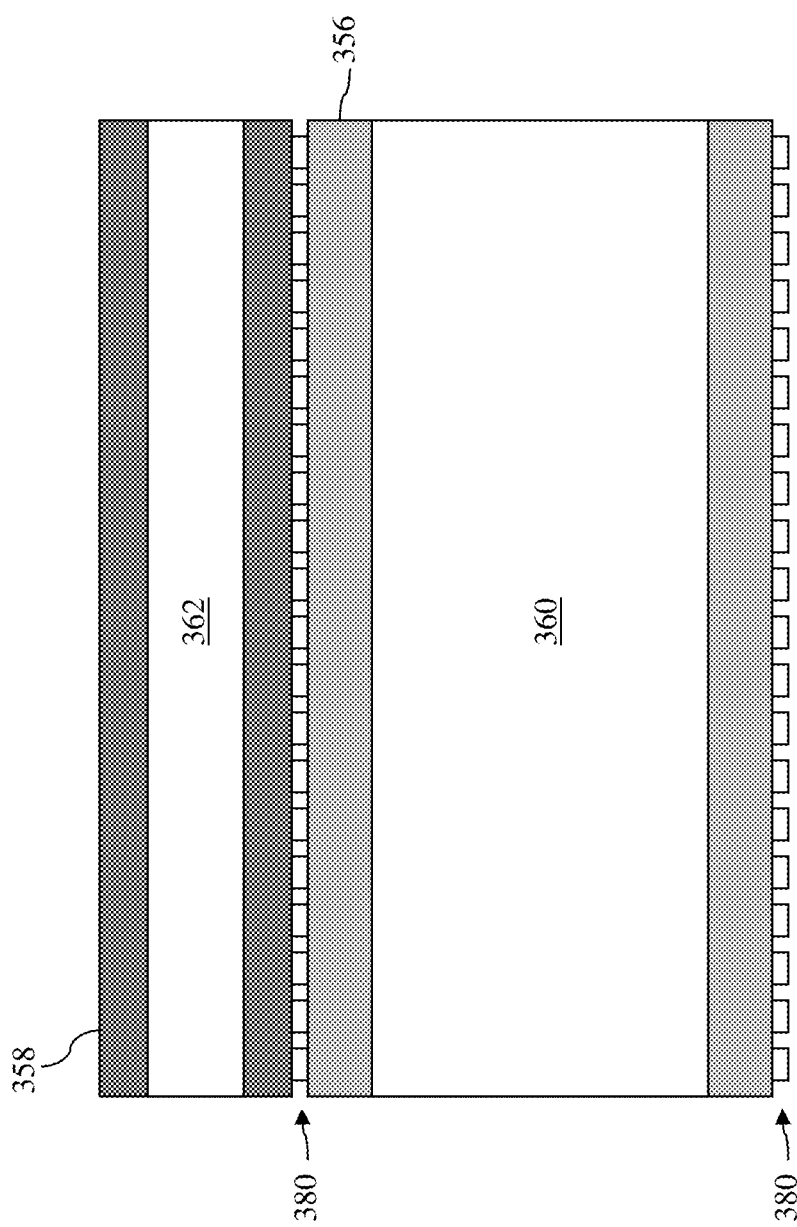
FIG. 27 is a diagrammatic cross-sectional side view of the separated components of FIG. 23 positioned together in preparation for forming the catheter according to another embodiment of the present disclosure.
Figure 28:
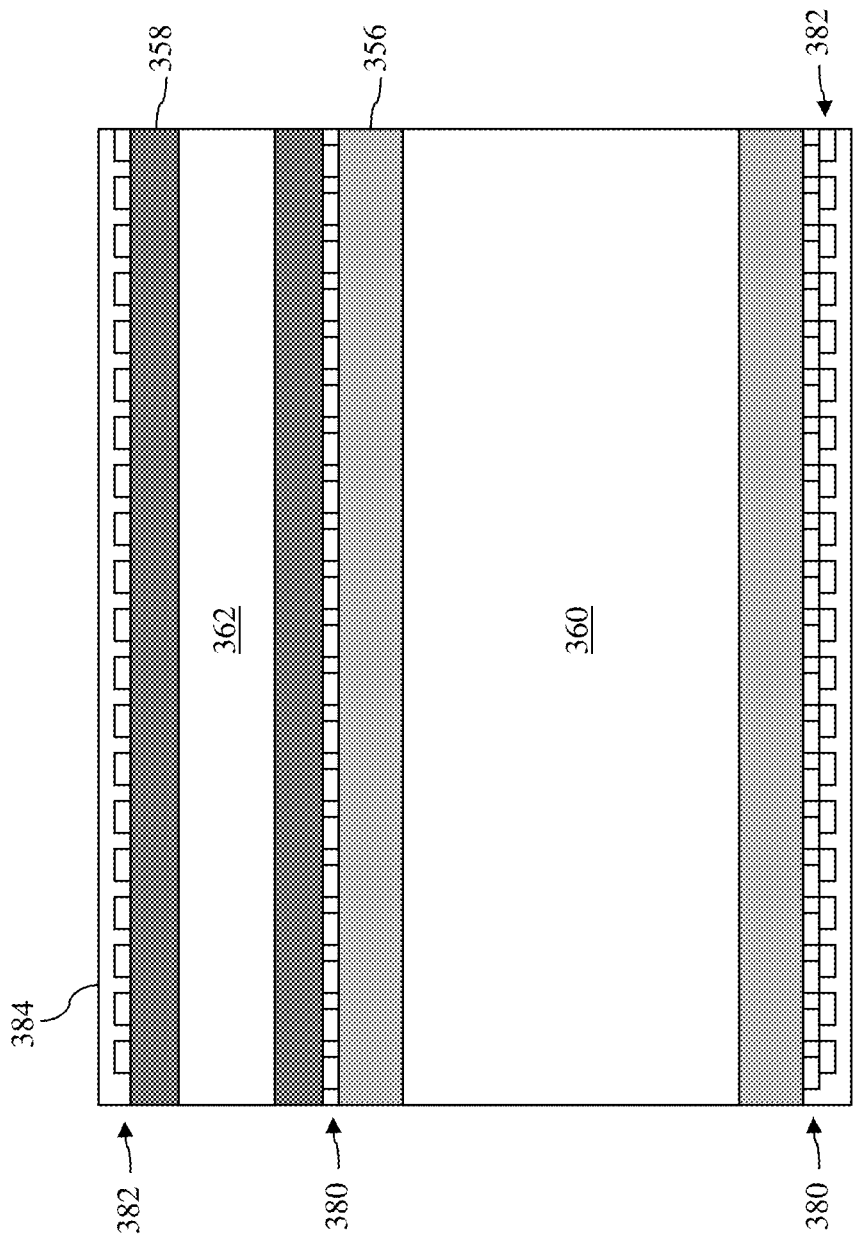
FIG. 28 is a diagrammatic cross-sectional side view similar to that of FIG. 27, but showing the separated components joined together to form the catheter.

Referring now to FIGS. 27 and 28, illustrated therein is another technique for securing the guiding body 358 to the main body 356. In that regard, as shown in FIG. 27 a first layer or winding 380 of filament has been placed around main body 356. For example, in some instances layer 380 is a first pass of the filament winding distally along the length of the main body. After the first pass and before the filament is wound back towards the proximal end of the main body, the guiding body 358 is positioned adjacent to the main body 356 and, in particular, is positioned in contact with the layer 380. With the guiding body 358 in position, the filament is wound proximally to make its second pass along the catheter. As a result, as shown in FIG. 28, the guiding body 358 is wrapped within the second layer 382 of the filament along with the main body 356. Accordingly, with the application of a polymer layer 384 over the first and second layers 380, 382, the guiding body 358 is imbedded therein and secured to the main body. In other instances, additional layers of windings and/or polymer can be added to further secure the guiding body 358 to the main body 356.

Figure 29:
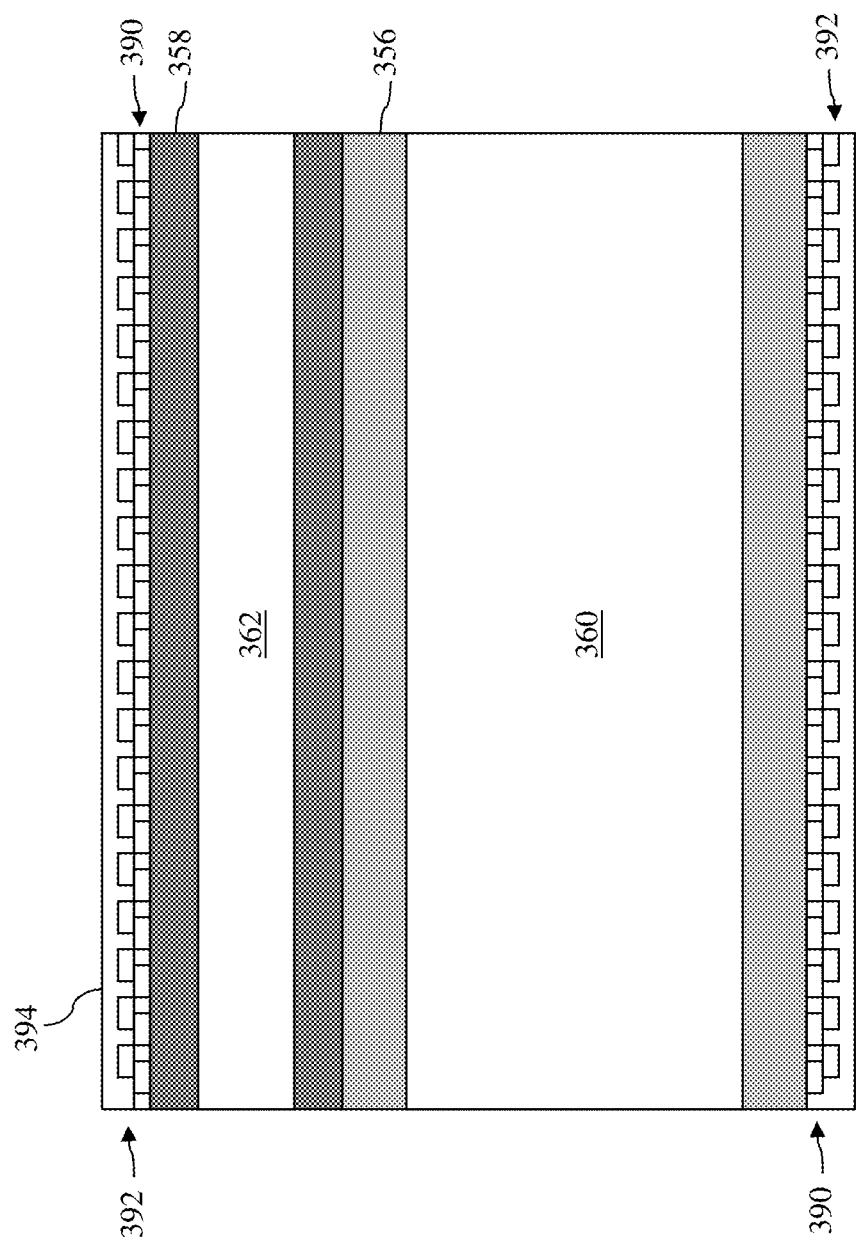
FIG. 29 is a diagrammatic cross-sectional side view of the separated components of FIG. 23 joined together to form a catheter according to another embodiment of the present disclosure.

Referring now to FIG. 29, illustrated therein is another technique for securing the guiding body 358 to the main body 356. As shown, the technique of FIG. 29 is similar to that of FIGS. 27 and 28, but instead of imbedding the guiding body 358 between passes of the filament, the guiding body 358 is positioned directly adjacent to the main body 356 and then a first pass 390 and a second pass 392 of the filament is made over both the guiding body 358 and the main body 356. Then, one or more polymer layers are sprayed over the layers 390 and 392 to fixedly secure the guiding body 358 to the main body 356.

After securing the guiding body 358 to the main body 356 using one or more of the techniques described above, the outer profile of the catheter 350 can be trimmed, smoothed, polished, and/or otherwise treated to achieve a desired profile. In that regard, one or more of mechanical and optical (e.g., laser) cutters can be utilized.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of manufacturing a catheter, comprising:
   manufacturing a first medical tubing having a proximal portion, a distal portion, and lumen extending along its length between the proximal portion and the distal portion, the first medical tubing formed of a first polymer having a first color;
   manufacturing a second medical tubing having a proximal portion, a distal portion, and a lumen extending along its length between the proximal portion and the distal portion, the second medical tubing formed of a second polymer having a second color different than the first color; and
   fixedly securing the second medical tubing to the first medical tubing, wherein the fixedly securing includes:
      positioning the second medical tubing adjacent to the first medical tubing such that the second medical tubing extends parallel to the distal portion of the first medical tubing;
      heating the first polymer having the first color of first medical tubing;
      heating the second polymer having the second color of second medical tubing; and
      applying at least one additional layer of polymer to the first and second medical tubings such that the at least one additional layer of polymer bonds with the heated first polymer having the first color and bonds with the heated second polymer having the second color, wherein the first and second medical tubings are embedded together within the at least one additional layer of polymer as a result of the applying, and wherein the at least one additional layer of polymer is translucent such that the different first and second colors of the respective first and second medical tubings are visible after the applying.

2. The method of claim 1, wherein fixedly securing the second medical tubing to the first medical tubing further comprises wrapping a filament around the first and second medical tubings.

3. The method of claim 2, wherein an additional layer of polymer is sprayed over the filament wrapped around the first and second medical tubings.

4. The method of claim 1, wherein each of the first and second medical tubings are not extruded.

5. A method of manufacturing a catheter, comprising:
   manufacturing a first medical tubing having a proximal portion, a distal portion, and lumen extending along its length between the proximal portion and the distal portion, the first medical tubing formed of a material having a first color;
   manufacturing a second medical tubing having a proximal portion, a distal portion, and a lumen extending along its length between the proximal portion and the distal portion, the second medical tubing formed of a material having a second color different than the first color; and
   fixedly securing the second medical tubing to the first medical tubing;
   wherein fixedly securing the second medical tubing to the first medical tubing comprises spraying at least one layer of polymer around the first and second medical tubings;

wherein fixedly securing the second medical tubing to the first medical tubing further comprises wrapping a filament around the first and second medical tubings; and wherein a layer of filament is positioned between the second medical tubing and the first medical tubing prior to wrapping the filament around the first and second medical tubings.

6. The method of claim 5, wherein the layer of filament positioned between the second medical tubing and the first medical tubing is wrapped around the first medical tubing.

7. The method of claim 6, wherein the layer of filament positioned between the second medical tubing and the first medical tubing is wrapped around the first medical tubing by a filament source moving in a first direction along a longitudinal axis of the first medical tubing.

8. The method of claim 7, wherein the filament wrapped around the first and second medical tubings is wrapped around the first and second medical tubings by the filament source moving a second direction along the longitudinal axis of the first medical tubing, the second direction being opposite the first direction.

9. A method of manufacturing a catheter, comprising:

manufacturing a first medical tubing having a proximal portion, a distal portion, and lumen extending along its length between the proximal portion and the distal portion, the first medical tubing formed of a material having a first color;

manufacturing a second medical tubing having a proximal portion, a distal portion, and a lumen extending along its length between the proximal portion and the distal portion, the second medical tubing formed of a material having a second color different than the first color;

wrapping a continuous filament around the first medical tubing during a first pass of the continuous filament along the length of the first medical tubing;

positioning the second medical tubing adjacent the distal portion of the first medical tubing;

wrapping the continuous filament around the first and second medical tubings during a second pass of the continuous filament along the length of the second medical tubing, wherein the second medical tubing is positioned adjacent the distal portion of the first medical tubing during the wrapping; and spraying at least one layer of polymer over the continuous filament wrapped around the first and second medical tubings.

10. The method of claim 9, wherein the at least one layer of polymer is translucent such that the different first and second colors of the respective first and second medical tubings are visible after the spraying.

* * * * *